(12) United States Patent
Feng et al.

(10) Patent No.: US 11,453,819 B2
(45) Date of Patent: Sep. 27, 2022

(54) VISCOELASTIC SURFACTANTS FOR SELF-DIVERTING ACID UNDER HIGH TEMPERATURE AND PREPARATION METHOD

(71) Applicant: SICHUAN UNIVERSITY, Chengdu (CN)

(72) Inventors: Yujun Feng, Chengdu (CN); Ji Wang, Chengdu (CN); Hongyao Yin, Chengdu (CN)

(73) Assignee: SICHUAN UNIVERSITY, Chengdu (CN)

( * ) Notice: Subject to any disclaimer, the term of this patent is extended or adjusted under 35 U.S.C. 154(b) by 0 days.

(21) Appl. No.: 17/293,486

(22) PCT Filed: May 16, 2019

(86) PCT No.: PCT/CN2019/087290
§ 371 (c)(1),
(2) Date: May 13, 2021

(87) PCT Pub. No.: WO2020/098240
PCT Pub. Date: May 22, 2020

(65) Prior Publication Data
US 2021/0355371 A1 Nov. 18, 2021

(30) Foreign Application Priority Data
Nov. 14, 2018 (CN) .......................... 201811350977.0

(51) Int. Cl.
*C07C 209/44* (2006.01)
*C09K 8/60* (2006.01)
*C09K 8/74* (2006.01)

(52) U.S. Cl.
CPC ............ *C09K 8/602* (2013.01); *C07C 209/44* (2013.01); *C09K 8/74* (2013.01); *C09K 2208/30* (2013.01)

(58) Field of Classification Search
None
See application file for complete search history.

(56) References Cited

U.S. PATENT DOCUMENTS 4,695,389 A 9/1987 Kubala
7,119,050 B2 10/2006 Chang et al.

FOREIGN PATENT DOCUMENTS

CN 101798274 A 8/2010
CN 102585797 A 7/2012
(Continued)

OTHER PUBLICATIONS

Yoshimura et al. (Langmuir, 2005, 21, 10409) (Year: 2005).*
(Continued)

*Primary Examiner* — Clinton A Brooks
*Assistant Examiner* — Jennifer C Sawyer
(74) *Attorney, Agent, or Firm* — Bayramoglu Law Offices LLC

(57) ABSTRACT

A viscoelastic surfactant (VES) for a self-diverting acid under high temperature has a structural formula shown as formula (I), wherein, n is saturated hydrocarbon with 2 to 8 carbon atoms; $R_1$ is saturated or unsaturated hydrocarbon with 18 to 28 carbon atoms; $R_2$ and $R_3$ are independently methyl, ethyl or hydrogen, and $R_2$ and $R_3$ can be the same or different; and $X^-$ is any one of $Cl^-$, $Br^-$, $CO_3^{2-}$, $SO_4^{2-}$, $HCOO^-$ and $CH_3COO^-$. The method for preparing the surfactant includes subjecting a fatty acid and an organic amine to acid-amine condensation to obtain an intermediate. The intermediate reacts with a metal hydride to obtain a fatty amine. Then, an acid solution is used to protonate the fatty (Continued)

amine to obtain an ultra-long-chain viscoelastic cationic surfactant. The present invention also provides use of the surfactant as a thickener for a self-diverting acid.

12 Claims, 10 Drawing Sheets

(56) References Cited

FOREIGN PATENT DOCUMENTS

| CN | 106995692 A | 8/2017 |
|----|-------------|--------|
| CN | 107088385 A | 8/2017 |
| CN | 109486476 A | 3/2019 |
| WO | 2017174424 A1 | 10/2017 |

OTHER PUBLICATIONS

Kirk M. Bartko, et al., Effective Matrix Acidizing in Carbonate Reservoir—Does Perforating Matter?, SPE Middle East Oil and Gas Show and Conference, 2007, pp. 1-10, SPE-105022-MS.
Frank Chang, et al., A Novel Self-Diverting-Acid Developed for Matrix Stimulation of Carbonate Reservoirs, Society of Petroleum Engineers, 2001, pp. 1-6, SPE 65033.
Yi Liu, et al., VDA Viscosity Mechanism, Natural Gas Industry, 2008, pp. 1-3, vol. 28 No. 11.
Zengying Zhao, et al., Performance of EDAB-HCl Acid Blended System as Fracturing Fluids in Oil Fields, Chinese Journal of Chemical Engineering, 2014, pp. 202-207, 22(2).
Jing Liu, et al., Development and Performance Evaluation of Clean Self-Steering Acid, Journal of Oil and Gas Technology, 2009, pp. 302-305, vol. 31 No. 3.

* cited by examiner

VISCOELASTIC SURFACTANTS FOR SELF-DIVERTING ACID UNDER HIGH TEMPERATURE AND PREPARATION METHOD

CROSS REFERENCE TO THE RELATED APPLICATIONS

This application is the national phase entry of International Application No. PCT/CN2019/087290, filed on May 16, 2019, which is based upon and claims priority to Chinese Patent Application No. 201811350977.0, filed on Nov. 14, 2018, the entire contents of which are incorporated herein by reference.

TECHNICAL FIELD

The present invention relates to the field of oil and gas production, and more particularly, to a class of viscoelastic surfactants (VES) for self diverting acid used in acidizing stimulation of high-temperature oil or gas reservoirs and a preparation method and use thereof.

BACKGROUND

In order to restore and improve the production of low-permeability oil and gas wells, an acid solution (generally 20 wt % HCl) is often injected into the reservoir to dissolve carbonates and clays, or the blockage within formation pores and fractures. This operation is known as acidizing stimulation, which restores the permeability of the reservoir and enlarges the oil and gas flow channels. However, two challenges have been presented in the conventional acid systems: rapid reaction of the acid with the reservoir rock leads to a short effective acidification distance, thus in-depth stimulation cannot be targeted; because of the heterogeneity of the reservoir and least resistance, the acid solution preferably goes into the high-permeability zones rather than the low-permeability ones which need to be treated first. Additionally, the follow-up acid solution will continue to flow along the highly permeably layers owing to the smaller flow resistance, rendering over-acidized of these zones; on the contrary, the low- and medium-permeability areas, have not been effectively deblocked, and eventually, the heterogeneity of the reservoir is even increased.

In order to solve the above problems, Schamberger pioneered in 2000 the utilization of viscoelastic surfactant (VES) as thickeners for conventional acid system to acidize carbonate reservoirs. When this highly viscous acid solution is pumped into the reservoir, the diffusion of $H^+$ to the rock surface is slowed down. As a result, the acid-rock reaction rate is decreased and the operation time of the acid solution in the reservoir is extended. Moreover, as the acid-rock reaction ($CaCO_3+2HCl=CaCl_2+H_2O+CO_2\uparrow$) proceeds, the concentration of HCl continuously decreases, the pH increases and metal ions ($Ca^{2+}$) are continuously produced, which further increases the viscosity of the acid system. This high-viscosity acid solution can not only further reduce the acid-rock reaction rate, but it also temporarily blocks the high-permeability area, forcing the follow-up acid solution to enter the low- and medium-permeability areas. Therefore, the diversion of an acid solution is implemented to achieve the twofold purposes of deep acidizing and uniform acidification in reservoirs. Such an acid system that can realize the automatic diversion of the acid solution only by the change of its own pH is called viscoelastic self-diverting acid (VDA).

Compared with other diverting acids, especially the cross-linked polymer acid system, the VDA system has two prominent advantages: (1) without a crosslinker of $Fe^{3+}$, $Zr^{4+}$ or other polyvalent metal ions, the metal hydroxide precipitation and the metal sulfide precipitation in sulfur-including wells will be avoided after the pH is increased because of the consumption of the acid solution. (2) When the VDA system encounters hydrocarbons in the reservoir, the hydrophobic cores of the wormlike micelles in the viscoelastic surfactant solution will be destroyed. This causes the three-dimensional network structure to dis-entangle and transform into spherical micelles, which results in the rapid reduction of the viscosity of the system, facilitates the flowback, and thus avoids a secondary damage and pollution to the reservoir. Since its introduction, the VDA system has become an area of special interest in the field of acidizing or acidizing-fracturing due to its superior diverting performance, fluid loss-reduction performance and non-damage to the reservoir. The VDA system has been successfully applied to the stimulation operation in the Middle East, South America, the Gulf of Mexico and other regions.

Nevertheless, the VDA system still has some disadvantages:

(1) The current VES is not stable under high temperatures and thus is only suitable for reservoirs below 120° C. One prior example includes a preparation of a self-diverting acid system with the combination of five percent (5%) betaine surfactants and 0.8 percent (0.8%) quaternary ammonium surfactants, which has a viscosity that increases first and then decreases with the increasing pH. The subject example exhibits the self-diverting performance, but has a viscosity only of 110 mPa·s at 95° C. Therefore, this system is only suitable for the acidizing of reservoirs at mild temperatures. A second example includes Chinese patent CN106995692A, which discloses a self-diverting acid based on the combination of VES and nanoparticles ($TiO_2$, $SiO_2$). Although this acid solution has advantages, such as a self-diverting performance, slow reaction rate and low fluid loss, no crosslinkers and gel breakers required for complete flowback, and no damage caused to the reservoirs, laboratory studies have found that this system has a viscosity of only of 30 mPa·s, however, after being sheared at 80° C. and 170 $s^{-1}$ for 1 h.

U.S. Pat. No. 4,695,389 discloses a VDA system based on N,N-dihydroxyethyl fatty amine acetate surfactant, which has a low initial viscosity. As the acid-rock reaction proceeds, the viscosity of this system increases resulting in a larger flow resistance, which forces the subsequently-injected acid solution to enter into low-permeability areas. The patented system can thus achieve the purpose of uniform acidizing. However, the system has a viscosity as low as 5 mPa·s at 80° C., making it ineffective to reduce the acid-rock reaction rate.

U.S. Pat. No. 7,119,050 discloses a VDA system based on an alkyl betaine amphoteric surfactant. As the acid-rock reaction proceeds, the viscosity of this system increases first and then decreases, and the viscosity is as high as 100 mPa·s at 150° C. However, the alkyl betaine surfactant is used at an amount as high as 8%, resulting in a high operation cost.

(2) The VESs used in the current VDA system are mostly cationic and zwitterionic surfactants, and especially alkyl betaine amphoteric surfactants, amine oxide amphoteric surfactants or the like. The molecular structures of these VESs typically include weak bonds susceptible to hydrolysis (amide bonds, ester bonds, ether bonds, etc.), which are easily broken in an environment with high temperature and strong acids. Therefore, during acidification, these VESs are difficult to maintain a stable chemical structure, and tend to deteriorate and decompose.

It is therefore highly desirable to develop a VES as a thickener for VDA, which can maintain a certain viscosity in a high temperature environment and have a stable structure.

SUMMARY

The present invention is intended to overcome the shortcomings of the prior art and provide a VES for a self-diverting acid under high temperature and a preparation method and use thereof. The new VES of the invention can maintain a stable chemical structure in an environment with strong acids and high temperature, has excellent acid solution-thickening performance and prominent temperature-resistance, thereby meeting the requirements for use in a harsh environment with strong acids, high temperature and the like.

The objective of the present invention is achieved by the following technical solutions. A VES for a self-diverting acid under high temperature is provided, and the VES has the following structural formula:

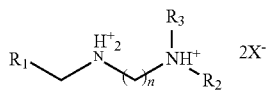

where, n is a saturated hydrocarbon with 2 to 8 carbon atoms; $R_1$ is a saturated or unsaturated hydrocarbon with 18 to 28 carbon atoms; $R_2$ and $R_3$ are independently methyl, ethyl or hydrogen, and $R_2$ and $R_3$ can be the same or different; and $X^-$ is any one of $Cl^-$, $Br^-$, $F^-$, $CO_3^{2-}$, $SO_4^{2-}$, $HCOO^-$ and $CH_3COO^-$.

A method for preparing the VES for a self-diverting acid under high temperature is provided, including the following steps:

S1: adding a fatty acid and an organic amine to a reactor, and heating the mixture to 160° C. to 170° C.; conducting reaction for 11 h to 13 h and then stopping the reaction; pouring the reaction solution into a cold acetone solution after the reaction solution is cooled to 25° C. to 35° C., and stirring the resulting solution; then conducting filtration, and washing the obtained solid 2 to 3 times with acetone; and conducting lyophilization to obtain a white solid intermediate; where the organic amine and the fatty acid are used at a molar ratio of (1.1-1.5):1;

S2: dissolving the obtained intermediate in tetrahydrofuran (THF), and adding the resulting solution dropwise to a solution of a metal hydride in THF at 0° C. to 5° C.; heating the resulting solution to 65° C. to 85° C., and conducting reaction for 24 h to 36 h; adding deionized water, a NaOH solution with a mass concentration of 10% to 20% and deionized water in sequence to the reaction solution after the reaction is completed; then conducting filtration, drying the filtrate, and conducting filtration for the filtrate once again; and removing the solvent from the filtrate obtained in the second filtration to obtain a fatty amine; where, the intermediate and the metal hydride are used at a molar ratio of 1:(2.0-2.5); and the deionized water is added the first time to quench the metal hydride, then the NaOH solution is added to remove metal ions, and then the deionized water is added the second time to ensure that the metal hydride is completely quenched; and S3: mixing the fatty amine with an acid solution having a mass concentration of 10% to 20%, and thoroughly stirring the resulting solution to protonate the tertiary fatty amine, namely, to form an ultra-long-chain VES, where the fatty amine has a molar ratio of 1:2 with hydrogen ions in the acid solution.

The fatty acid is a combination of at least one or more of saturated or unsaturated alkyl fatty acids that have 18 to 28 carbon atoms.

The organic amine includes a combination of one or more of N,N-dimethylethylenediamine, N,N-dimethyl-1,3-propanediamine, N,N-dimethyl-1,4-butanediamine, N,N-diethylethylenediamine N,N-diethyl-1,3-propanediamine, ethylenediamine, propanediamine, butanediamine, pentanediamine, hexamethylenediamine, heptanediamine and octanediamine.

The metal hydride includes a combination of one or more of $LiAlH_4$, $LiBH_4$ and $NaBH_4$.

The acid solution includes a combination of one or more of a HCl solution, a HBr solution, a HF solution, a $H_2SO_4$ solution, a $H_2CO_3$ solution, a HCOOH solution and a $CH_3COOH$ solution.

During the reaction, circulating water cooling is continuously conducted to have the organic amine refluxed.

Use of the VES for a self-diverting acid under high temperature as a thickener is provided.

The VES is mixed with an acid solution having a mass concentration of 10% to 20%, where, the acid solution having a mass concentration of 10% to 20% includes a combination of one or more of a HCl solution, a HBr solution, a HF solution, a $H_2SO_4$ solution, a $H_2CO_3$ solution, a HCOOH solution and a $CH_3COOH$ solution, and the 10% to 20% acid solution is used at an amount that allows the ultra-long-chain VES thickener to have a mass concentration of 1% to 3% in the obtained viscous acid solution.

The present invention has the following beneficial effects:

(1) The VES, as a thickener, has both excellent acid solution-thickening performance and prominent temperature-resistance. When the temperature is up to 150° C., a self-diverting acid based on the surfactant has a viscosity that is relatively stable and greater than 80 mPa·s, which meets the requirements for use in a harsh environment with strong acids, high temperature and the like.

(2) The VES, as a thickener, has a stable chemical structure, and does not decompose even in a harsh environment with high temperature, strong acids and the like, which meets the requirements for use in a harsh environment with strong acids, high temperature and the like.

(3) The VES, as a thickener, can significantly slow the reaction of the acid solution with the reservoir rock to achieve the purpose of extending the acidification distance, increasing the acidification time and uniform acidification.

(4) When the VES is used as a thickener in a self-diverting acid, an excellent viscosity-increasing effect can be achieved at a mass concentration of 1% for the VES, which make it inexpensive to produce on a large scale.

(5) In the preparation of the VES, the performance of the ultra-long-chain VES thickener can be adjusted by changing the types of the fatty acid, the fatty organic amine and the acid solution.

DETAILED DESCRIPTION OF THE EMBODIMENTS

Figure 1:
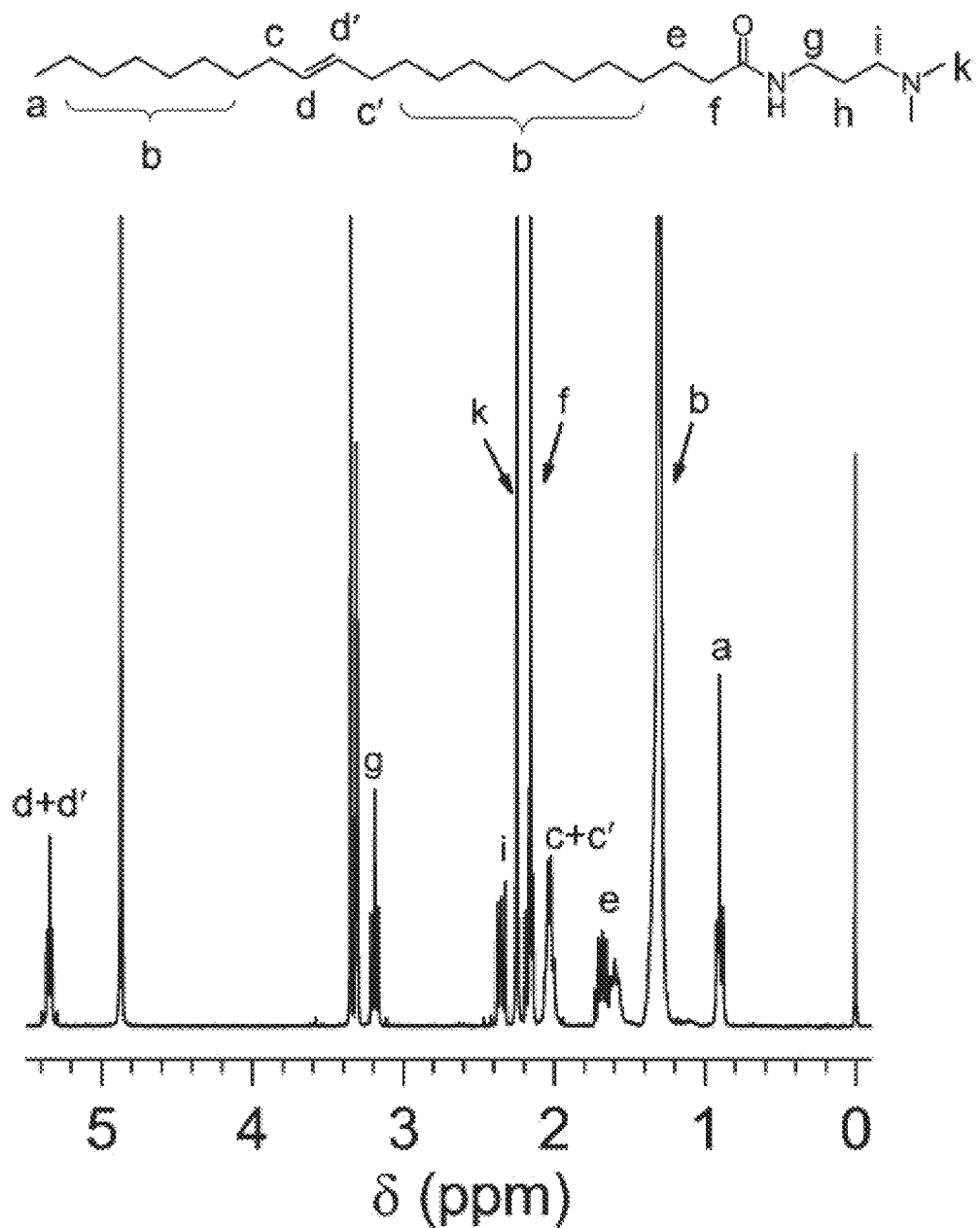
FIG. 1 is a $^1H$ NMR spectrum for N-(cis-docosa-9-alkenyl-amidopropyl)-N,N-dimethyl tertiary amine.
Figure 2:
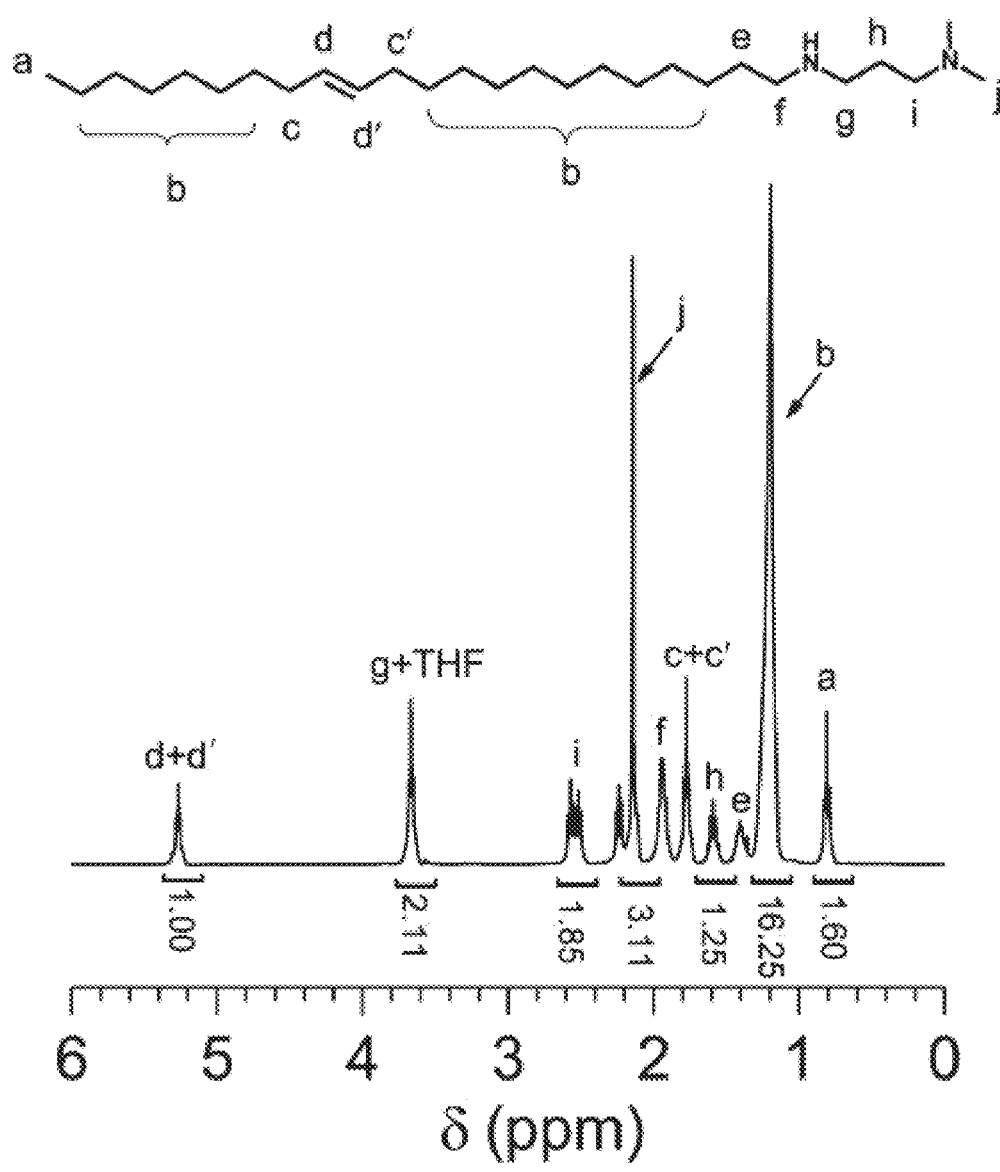
FIG. 2 is a $^1H$ NMR spectrum for N-(cis-docosa-9-alkenyl-aminopropyl)-N,N-dimethyl tertiary amine.
Figure 3:
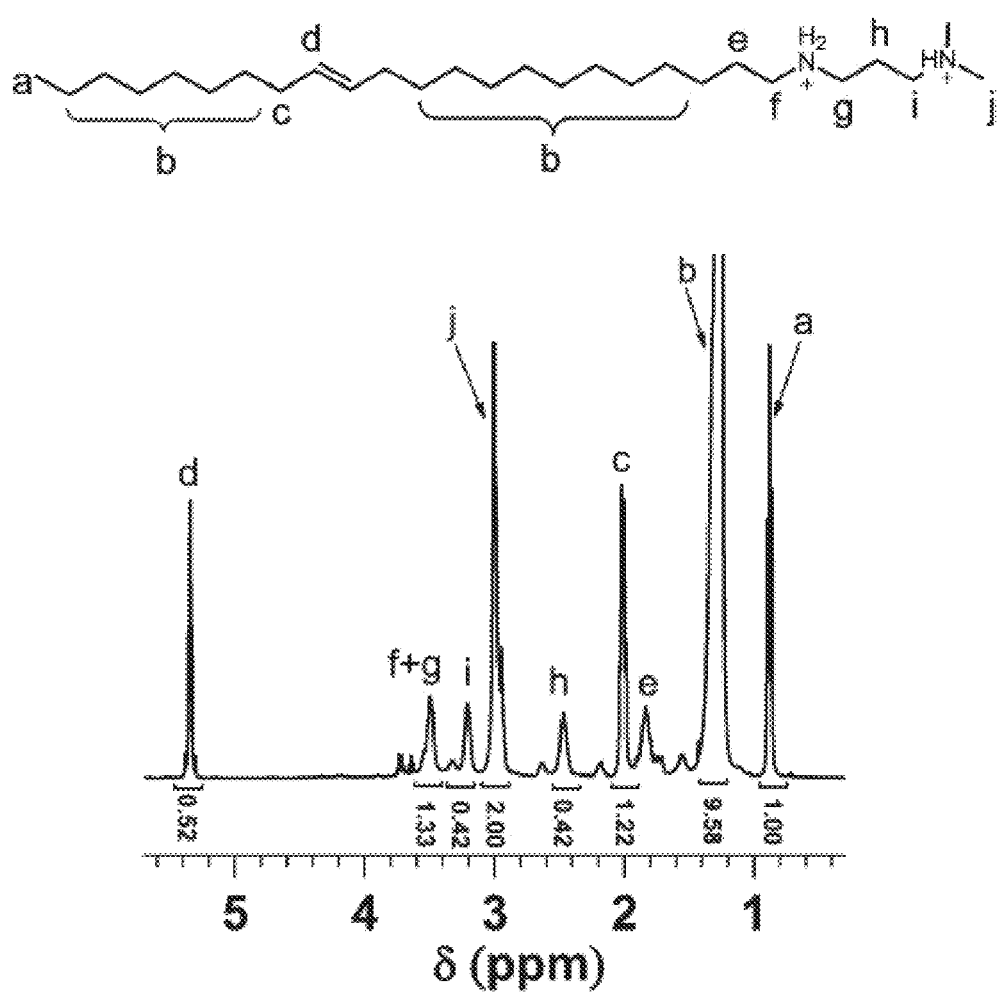
FIG. 3 is a $^1$H NMR spectrum for N-(cis-docosa-9-alkenyl-aminopropyl)-N,N-dimethyl tertiary amine hydrochloride.
Figure 4:
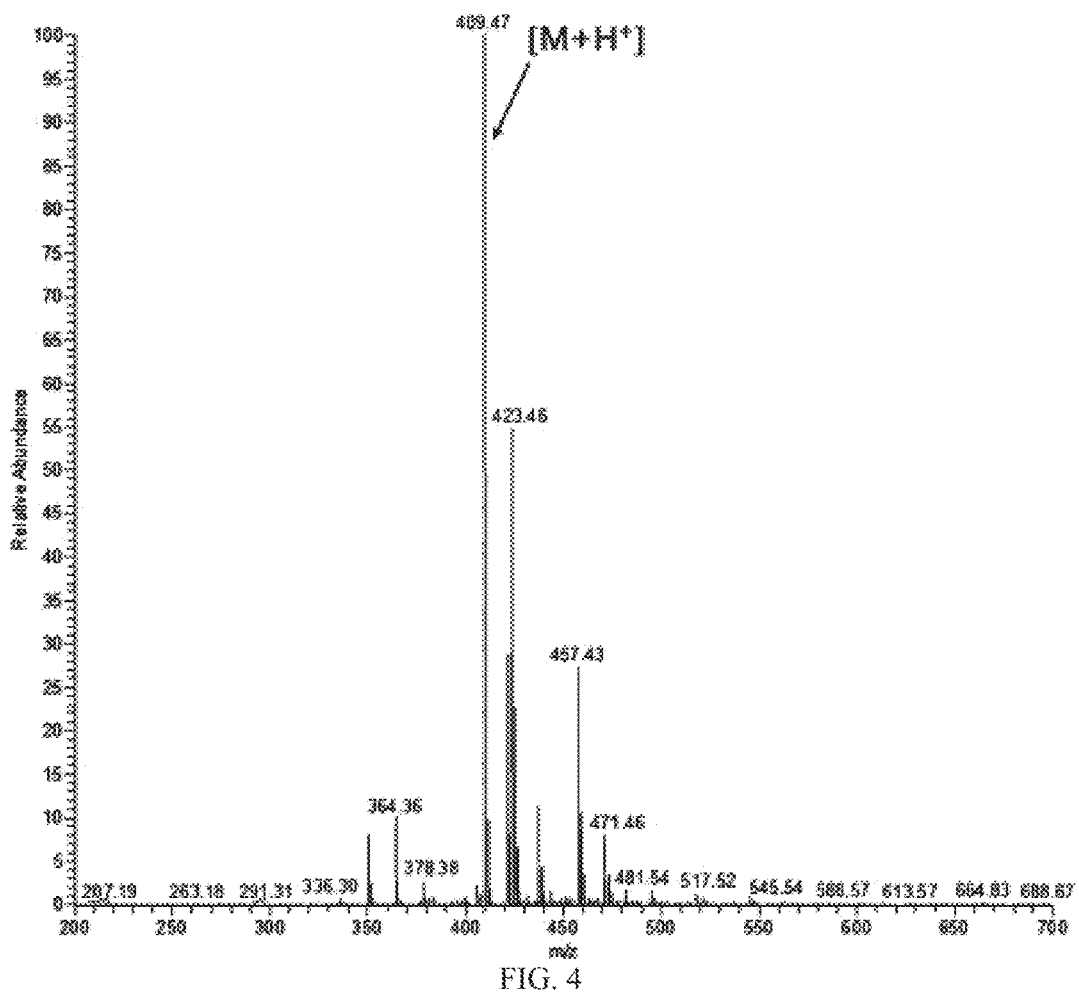
FIG. 4 is a mass spectrum for N-(cis-docosa-9-alkenyl-aminopropyl-N,N-dimethyl tertiary amine hydrochloride.

The technical solution in the present invention will be clearly and completely described below in conjunction with examples. The described examples are merely some rather than all of the examples of the present invention. All other examples obtained by those skilled in the art based on the examples of the present invention without creative efforts shall fall within the protection scope of the present invention.

As shown in FIGS. 1 to 12, a VES for a self-diverting acid under high temperature is provided, with the following structural formula:

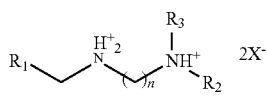

where, n is saturated hydrocarbon with 2 to 8 carbon atoms; $R_1$ is saturated or unsaturated hydrocarbon with 18 to 28 carbon atoms; $R_2$ and $R_3$ are independently methyl, ethyl or hydrogen, and $R_2$ and $R_3$ can be the same or different; and $X^-$ is any one of $Cl^-$, $Br^-$, $F^-$, $CO_3^{2-}$, $SO_4^{2-}$, $HCOO^-$ and $CH_3COO^-$.

A method for preparing the VES for a self-diverting acid under high temperature is also provided. The method includes the following steps:

S1: A fatty acid and an organic amine are added to a reactor, and the mixture is heated to 160° C. to 170° C. and then reacts for 11 h to 13 h; the reaction is stopped, and the reaction solution is poured into a cold acetone solution after the reaction solution is cooled to 25° C. to 35° C.; the resulting solution is stirred and filtrated; and the obtained solid is washed 2 to 3 times with acetone, and lyophilized to obtain a white solid intermediate. During the reaction, circulating water cooling is continuously conducted to have the organic amine refluxed. The organic amine and the fatty acid are used at a molar ratio of (1.1-1.5):1.

The fatty acid is a combination of at least one or more of saturated or unsaturated alkyl fatty acids that have 18 to 28 carbon atoms. The organic amine includes a combination of one or more of N,N-dimethylethylenediamine, N,N-dimethyl-1,3-propanediamine, N,N-dimethyl-1,4-butanediamine, N,N-diethylethylenediamine, N,N-diethyl-1,3-propanediamine, ethylenediamine, propanediamine, butanediamine, pentanediamine, hexamethylenediamine, heptanediamine and octanediamine.

S2: The obtained intermediate is dissolved in THF, and the resulting solution is added dropwise to a solution of a metal hydride in THF at 0° C. to 5° C.; the resulting solution is heated to 65° C. to 85° C. and then reacts for 24 h to 36 h; deionized water, a NaOH solution with a mass concentration of 10% to 20% and deionized water are added in sequence to the reaction solution after the reaction is completed; the resulting solution is filtrated, and the filtrate is dried and filtrated once again; and the solvent is removed from the filtrate obtained in the second filtration to obtain a fatty amine. The intermediate and the metal hydride are used at a molar ratio of 1:(2.0-2.5). The deionized water is added the first time to quench the metal hydride, then the NaOH solution is added to remove metal ions, and then the deionized water is added the second time to ensure that the metal hydride is completely quenched. The metal hydride includes a combination of one or more of $LiAlH_4$, $LiBH_4$ and $NaBH_4$.

S3: The fatty amine is mixed with an acid solution having a mass concentration of 10% to 20%, and the resulting solution is thoroughly stirred to protonate the tertiary fatty amine, namely, to form an ultra-long-chain VES. The fatty amine has a molar ratio of 1:2 with hydrogen ions ($H^+$) in the acid solution. The acid solution includes a combination of one or more of a HCl solution, a HBr solution, a HF solution, a $H_2SO_4$ solution, a $H_2CO_3$ solution, a HCOOH solution and a $CH_3COOH$ solution.

In the preparation of the VES, the performance of the ultra-long-chain VES thickener can be adjusted by changing the types of the fatty acid, the organic amine and the acid solution.

Use of the VES for a self-diverting acid under high temperature as a thickener is provided.

The VES is mixed with an acid solution having a mass concentration of 10% to 20%, where the acid solution having a mass concentration of 10% to 20% includes a combination of one or more of a HCl solution, a HBr solution, a HF solution, a $H_2SO_4$ solution, a $H_2CO_3$ solution, a HCOOH solution and a $CH_3COOH$ solution, and the ultra-long-chain VES thickener has a mass concentration of 1% to 3% in the obtained viscous acid solution.

When the VES is used as a thickener in a self-diverting acid, an excellent viscosity-increasing effect can be achieved at a mass concentration of 1% for the VES, which results in a low economic cost and is in favor of the large-scale use.

The VES, as a thickener, has both excellent acid solution-thickening performance and prominent temperature-resistance. When the temperature is up to 150° C., a self-diverting acid based on the surfactant has a viscosity that is relatively stable and greater than 80 mPa·s, which can meet the requirements for use in a harsh environment with strong acids, high temperature and the like.

The strong acid-resistance and high temperature-resistance properties are analyzed for the VES as a thickener below in conjunction with typical examples:

Example 1

(1) 16.92 g (0.05 mol) of cis-13-docosenoic acid (commonly known as "erucic acid") and 7.66 g (0.075 mol) of N,N-dimethylpropanediamine (n=2, $R_2$ and $R_3$ were methyl groups) were weighed and added to a three-necked flask, and the mixture was gradually heated to 160° C. and reacted for 11 h; then the reaction was stopped, and the reaction solution was transferred to an acetone solution after the reaction solution was cooled to room temperature; and the resulting solution was stirred, filtered, and lyophilized to obtain a white solid powder, namely, N-(cis-docosa-13-alkenyl-amidopropyl)-N,N-dimethyl tertiary amine, with structural characterization shown as $^1$H NMR spectrum (FIG. 1). The chemical shift of each proton peak for the compound had been found in the spectrum, and the integral area ratio of proton resonance peaks was in excellent agreement with the theoretical value, indicating that the compound had been successfully synthesized.

(2) The obtained N-(cis-docosa-13-alkenyl-amidopropyl)-N,N-dimethyl tertiary amine was added to a 500 mL round-bottom flask, and 100 mL of THF was added to dissolve the solid; and after the solid was completely dissolved, the resulting solution was cooled to 0° C., and a solution of $LiAlH_4$ in THF was added dropwise; then the mixture was heated to 85° C. and reacted for 24 h; after the reaction was completed, deionized water, a 10% NaOH solution, and deionized water were added in sequence to the obtained reaction solution to quench the reaction; the resulting solution was filtered, and the filtrate was dried over anhydrous $MgSO_4$ and filtered once again; and the final filtrate was subjected to rotary evaporation to remove the solvent to obtain N-(cis-docosa-13-alkenyl-aminopropyl)-N,N-dimethyl tertiary amine, with structural characterization shown as $^1$H NMR spectrum (FIG. 2), where the N-(cis-docosa-13-alkenyl-amidopropyl)-N,N-dimethyl tertiary amine and the metal hydride were used at a molar ratio of 1:2.5. The chemical shift of each proton peak for the compound had been found in the spectrum, and the integral area ratio of proton resonance peaks was in excellent agreement with the theoretical value, indicating that the compound had been successfully synthesized.

Figure 5:
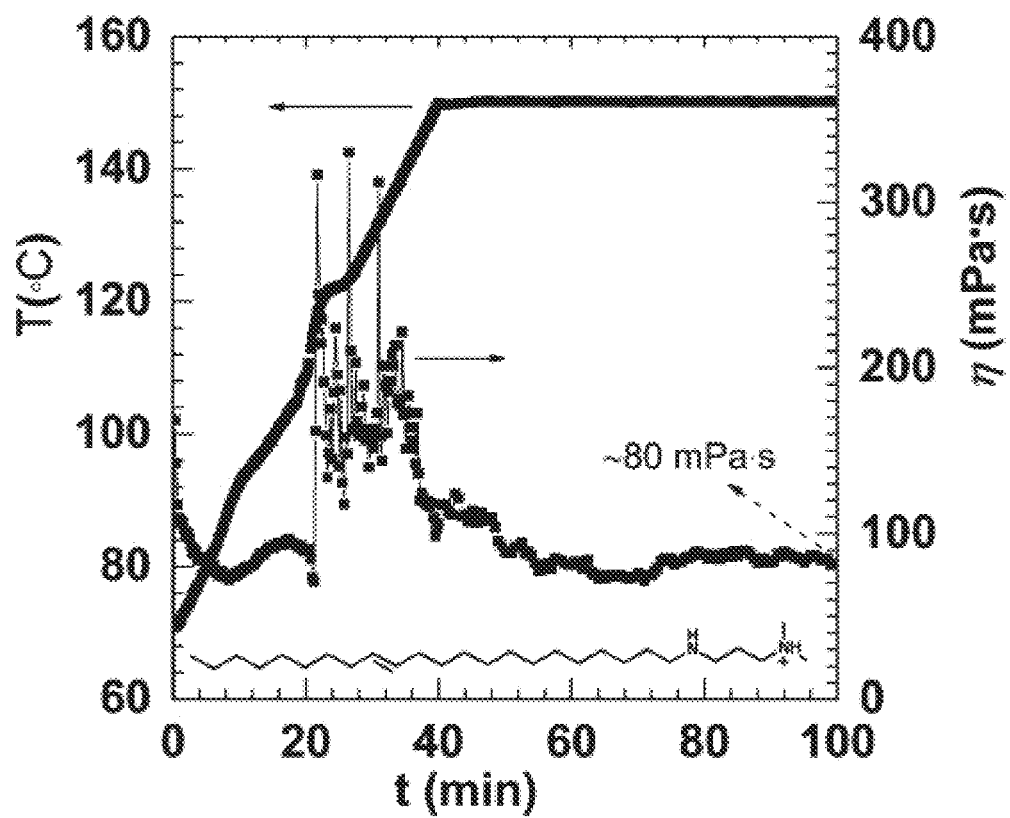
FIG. 5 shows the theological behavior of a 3.0% N-(cis-docosa-9-alkenyl-aminopropyl)-N,N-dimethyl tertiary amine sulfate solution in a 10% $H_2SO_4$ solution at 150° C.
Figure 6:
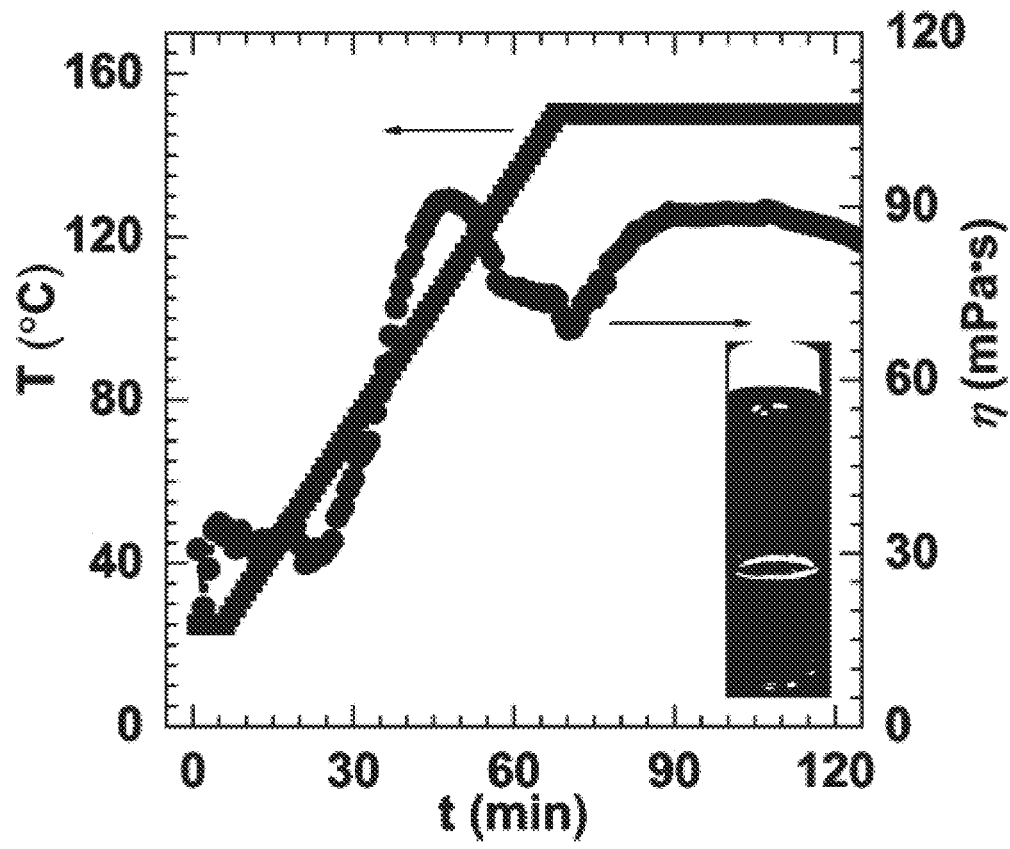
FIG. 6 shows the theological behavior of a 1.0% N-(cis-docosa-9-alkenyl-aminopropyl)-N,N-dimethyl tertiary amine hydrochloride solution in a 20% HCl solution at 150° C.
Figure 7:
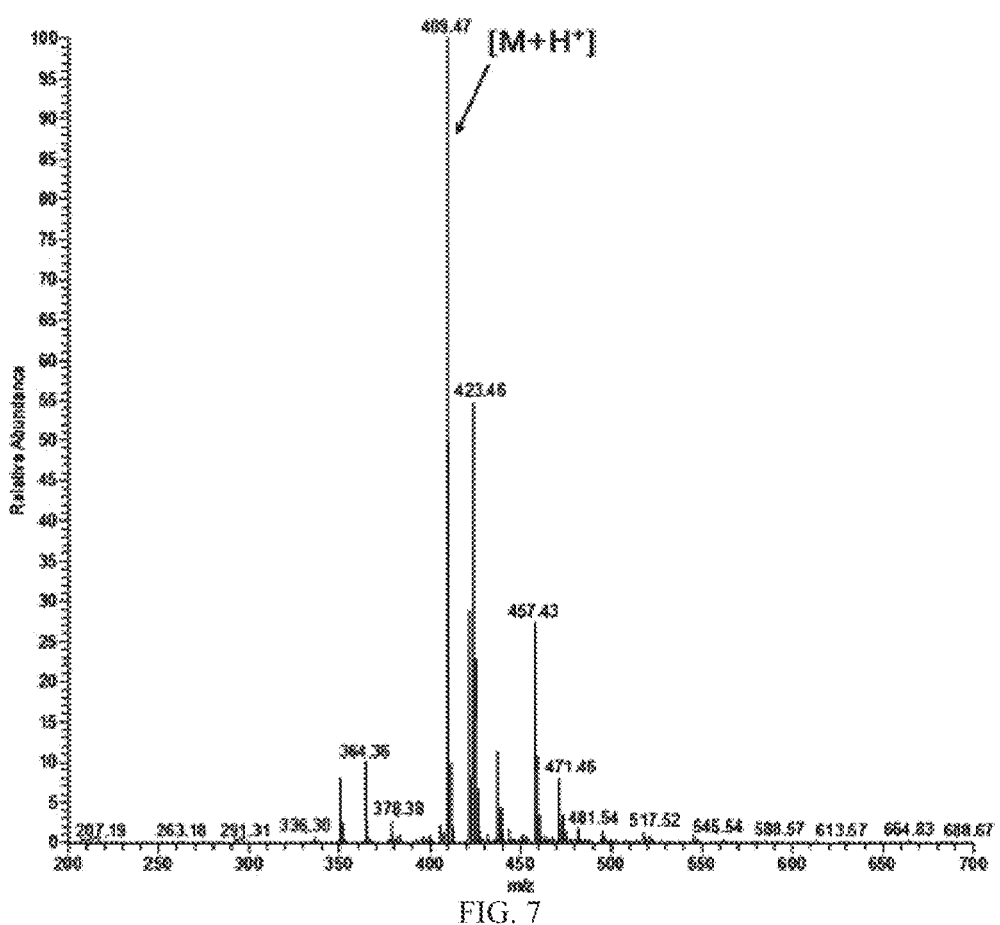
FIG. 7 is a mass spectrum for N-(cis-docosa-9-alkenyl-aminopropyl)-N,N-dimethyl tertiary amine hydrochloride that has been tested at 150° C. for viscosity.
Figure 8:
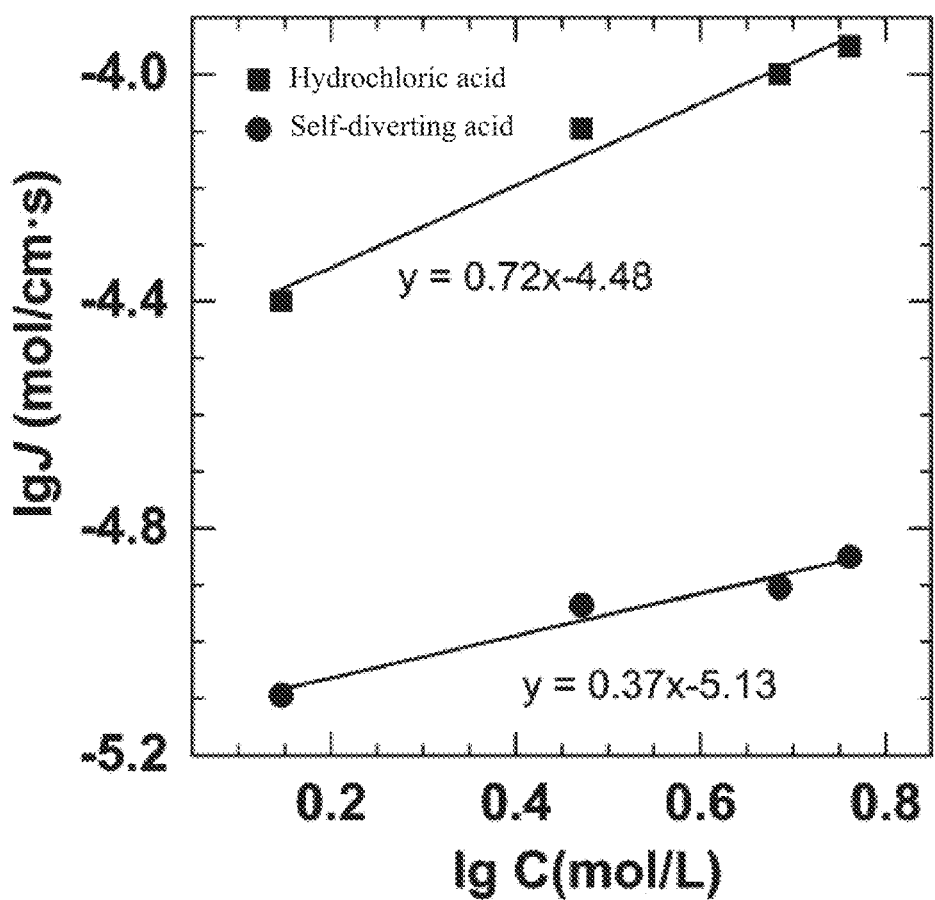
FIG. 8 shows the acid-rock reaction kinetic curve for a 3.0% N-(cis-docosa-9-alkenyl-aminopropyl)-N,N-dimethyl tertiary amine hydrochloride solution in a 20% HCl solution at 150° C.

(3) Temperature-resistance and shear-resistance test: N-(cis-docosa-13-alkenyl-aminopropyl)-N,N-dimethyl tertiary amine was mixed with a 10% $H_2SO_4$ solution and a 20% HCl solution separately, where, N-(cis-docosa-13-alkenyl-aminopropyl)-N,N-dimethyl tertiary amine had a molar ratio of 1:2 with $H^+$ in the 10% $H_2SO_4$ or 20% HCl solution. The resulting mixtures were thoroughly stirred at 50° C. for 24 h to obtain N-(cis-docosa-13-alkenyl)-N,N-dimethyl tertiary amine sulfate and N-(cis-docosa-13-alkenyl)-N,N-dimethyl tertiary amine hydrochloride (where, N-(cis-docosa-13-alkenyl)-N,N-dimethyl tertiary amine hydrochloride had structural characterization shown as the $^1$H NMR spectrum of FIG. 3 and the mass spectrum of FIG. 4), respectively. Then, the N-(cis-docosa-13-alkenyl)-N,N-dimethyl tertiary amine sulfate and N-(cis-docosa-13-alkenyl)-N,N-dimethyl tertiary amine hydrothloride were respectively mixed with a 15% $H_2SO_4$ solution and a 10% HCl solution to obtain a self-diverting acid of N-(cis-docosa-13-alkenyl)-N,N-dimethyl tertiary amine sulfate and a self-diverting acid of N-(cis-docosa-13-alkenyl)-N,N-dimethyl tertiary amine hydrochloride, where the N-(cis-docosa-13-alkenyl)-N,N-dimethyl tertiary amine sulfate and N-(cis-docosa-13-alkenyl)-N,N-dimethyl tertiary amine hydrothioride had a concentration of 3% and 1% in the respective acid solutions. The viscosity of the acid system was tested at different temperatures by Haake rheometer and the supporting PZ39 rotor/drum system thereof. The relationship of the viscosity of the obtained self-diverting acid system with temperature and time was tested at a shear rate of 170 s$^{-1}$. The results are shown in FIG. 5 and FIG. 6. It can be seen that, when the temperature is stabilized at 150° C., the viscosity of the acid solution is relatively stable and greater than 80 mPa·s, indicating that the ultra-long-chain VES obtained in this example has excellent temperature-resistance and shear-resistance as a thickener. After the test was completed, the acid solution was recovered. The resulting acid solution, which had the same appearance (colorless and transparent) as the acid solution before test, was lyophilized for mass spectrometry (FIG. 7). There is m/z=409.47 (M+H$^+$) in the spectrum, which has a theoretical value of 409.45, demonstrating that the ultra-long-chain surfactant prepared in this example has a stable chemical structure and does not decompose and deteriorate in an environment with high temperature and strong acids.

Figure 9:
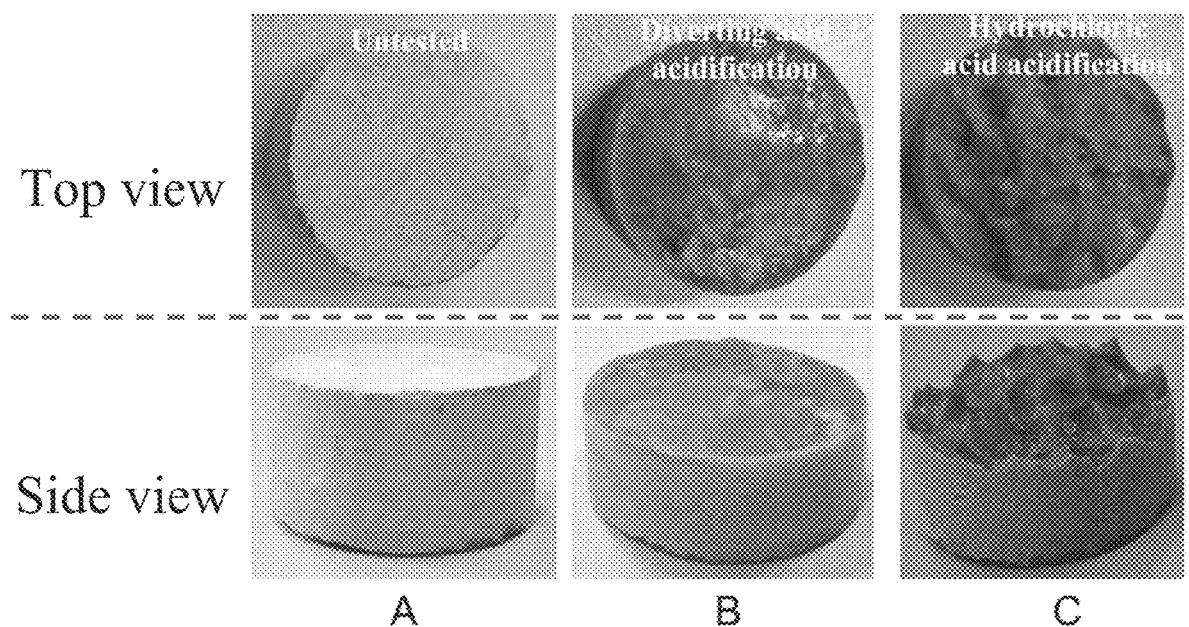
FIG. 9 shows contrast images of a Xinjiang outcrop before and after an acid-rock reaction.
Figure 10:
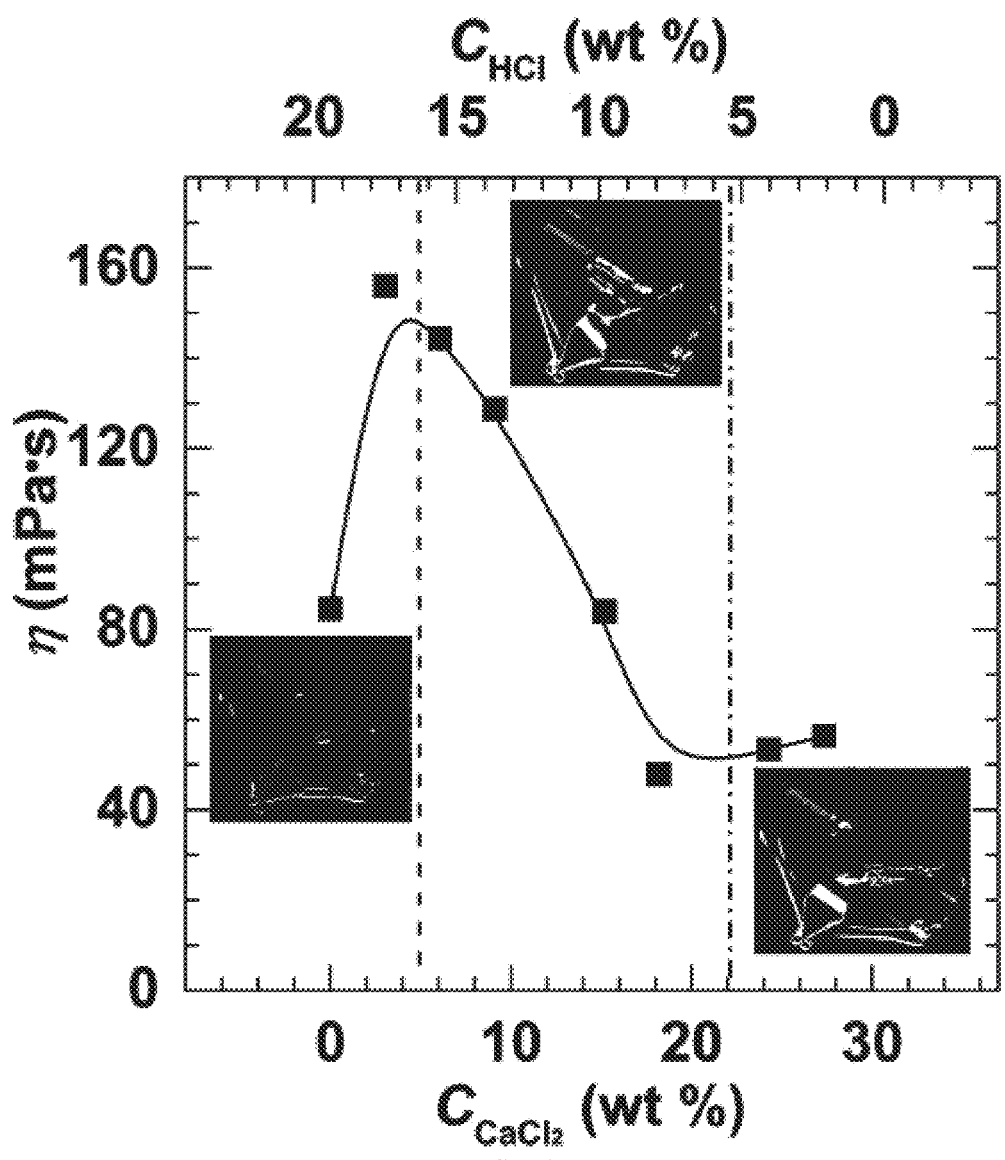
FIG. 10 is a plot showing the viscosity of N-(cis-docosa-9-alkenyl-aminopropyl)-N,N-dimethyl tertiary amine hydrochloride that changes with the varying contents of HCl and $CaCl_2$ in the acid solution at 150° C.
Figure 11:
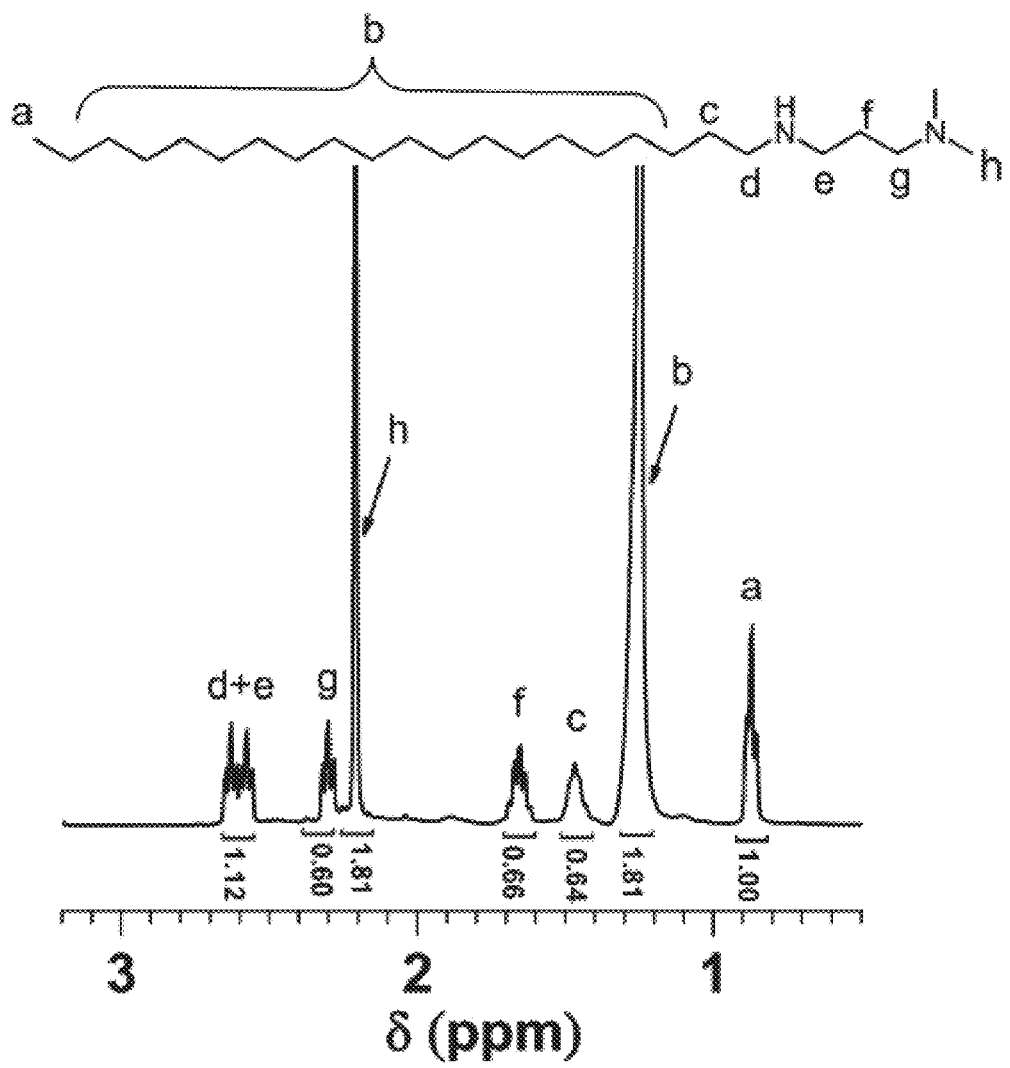
FIG. 11 is a $^1$H NMR spectrum for N-(octadecylaminopropyl)-N,N-dimethyl tertiary amine.

(4) Acid-rock reaction kinetics test: N-(cis-docosa-13-alkenyl-aminopropyl)-N,N-dimethyl tertiary amine was mixed with a 20% HCl solution, and the mixture was thoroughly stirred at 50° C. for 24 h to obtain a self-diverting acid of N-(cis-docosa-13-alkenyl-aminopropyl)-N,N-dimethyl tertiary amine hydrochloride. A Xinjiang outcrop with a cross-sectional area of 4.9 cm$^2$ was adopted, and the acid-rock reaction kinetics test was conducted by a rotating disk reactor, with a temperature of 150° C., a pressure of 7.5 MPa and a rotational speed of 500 r/min. It can be seen from the results that the self-diverting acid has a reaction rate constant of K=7.4×10$^{-6}$ (mol·L)$^{-m}$·mol/(cm$^2$·s), which is lower than that (K=3.5×10$^{-5}$ (mol·L)$^{-m}$·mol/(cm$^2$·s)) of the control group (20% HCl) (FIG. 8), indicating that the self-diverting acid solution with ultra-long-chain VES as a thickener in this example has excellent rate-reducing performance, and can effectively extend the acidification time. The outcrop samples were observed after the test. Compared with the outcrop corroded by 20% HCl, the outcrop corroded by the self-diverting acid solution with ultra-long-chain VES as a thickener in this example has uniform and smooth appearance, without obvious pitting corrosion, indicating that the self-diverting acid solution of this example has the ability to achieve uniform acidification. The details are shown in FIG. 9, where A shows the outcrop before the test, and B shows the outcrop reacted with a 20% HCl solution of N-(cis-docosa-13-alkenyl-aminopropyl)-N,N-dimethyl tertiary amine hydrochloride, and C shows the outcrop reacted with 20% HCl.

(5) Diverting ability test: In order to determine the variation tendency of the viscosity of the diverting acid in the reservoir, the concentrations of HCl and $CaCl_2$ were calculated at different time points during the acid-rock reaction. A series of mixed solutions of HCl and $CaCl_2$ were prepared, N-(cis-docosa-13-alkenyl-aminopropyl)-N,N-dimethyl tertiary amine was mixed with the above mixed solution of HCl and $CaCl_2$, and the resulting mixture was thoroughly stirred at 50° C. for 24 h. The diverting ability was tested by Anton Paar rheometer and the supporting PR170/XL rotor/drum system thereof. With a temperature of 150° C., a shear rate of 170 s$^{-1}$ and a pressure of 1 MPa, the viscosity of the self-diverting acid was determined at different time points. It can be seen from the results that the self-diverting acid based on N-(cis-docosa-13-alkenyl)-N,N-dimethyl tertiary amine hydrochloride has a viscosity which increases first and then decreases with the decreasing HCl concentration and the increasing $Ca^{2+}$ concentration (FIG. 10), indicating that the self-diverting acid solution with ultra-long-chain VES as a thickener in this example has excellent diverting performance and thus can achieve the uniform acidification in a target reservoir.

It can be seen from Example 1 that the surfactant, as a thickener, has a stable chemical structure, and does not decompose even in a harsh environment with high temperature, strong acids or the like, which meets the requirements for use in a harsh environment with strong acids, high temperature or the like. The surfactant, as a thickener, can significantly slow the reaction of the acid solution with the formation rock to achieve the purpose of extending the acidification distance, increasing the acidification time, and uniform acidification.

Example 2

(1) 14.22 g (0.05 mol) of octadecanoic acid (commonly known as "stearic acid") and 5.61 g (0.055 mol) of N,N-dimethylpropanediamine (n=2, $R_2$ and $R_3$ were methyl groups) were weighed and added to a three-necked flask, and the mixture was gradually heated to 170° C. and reacted for 13 h; then the reaction was stopped, and the reaction solution was transferred to an acetone solution after the reaction solution was cooled to room temperature; and the resulting solution was stirred, filtered, and lyophilized to obtain a white solid powder, namely, N-(octadecylamidopropyl)-N,N-dimethyl tertiary amine.

(2) The obtained N-(octadecylamidopropyl)-N,N-dimethyl tertiary amine was added to a 500 mL round-bottom flask, and 100 mL of THF was added to dissolve the solid. After the solid was completely dissolved, the resulting solution was cooled to 5° C. and a solution of $LiAlH_4$ in THF was added dropwise. The mixture was then heated to 65° C. and reacted for 36 h. After the reaction was completed, deionized water, a 10% NaOH solution and deionized water were added in sequence to the obtained reaction solution to quench the reaction. The resulting solution was filtered and the filtrate was dried over anhydrous $MgSO_4$ and filtered once again. The final filtrate was subjected to rotary evaporation to remove the solvent to obtain N-(octadecylaminopropyl)-N,N-dimethyl tertiary amine, with structural characterization shown as $^1H$ NMR spectrum (FIG. 11), where the N-(octadecylamidopropyl)-N,N-dimethyl tertiary amine and the metal hydride were used at a molar ratio of 1:2. The chemical shift of each proton peak for the compound had been found in the spectrum, and the integral area ratio of proton resonance peaks was in excellent agreement with the theoretical value, indicating that the compound had been successfully synthesized.

Figure 12:
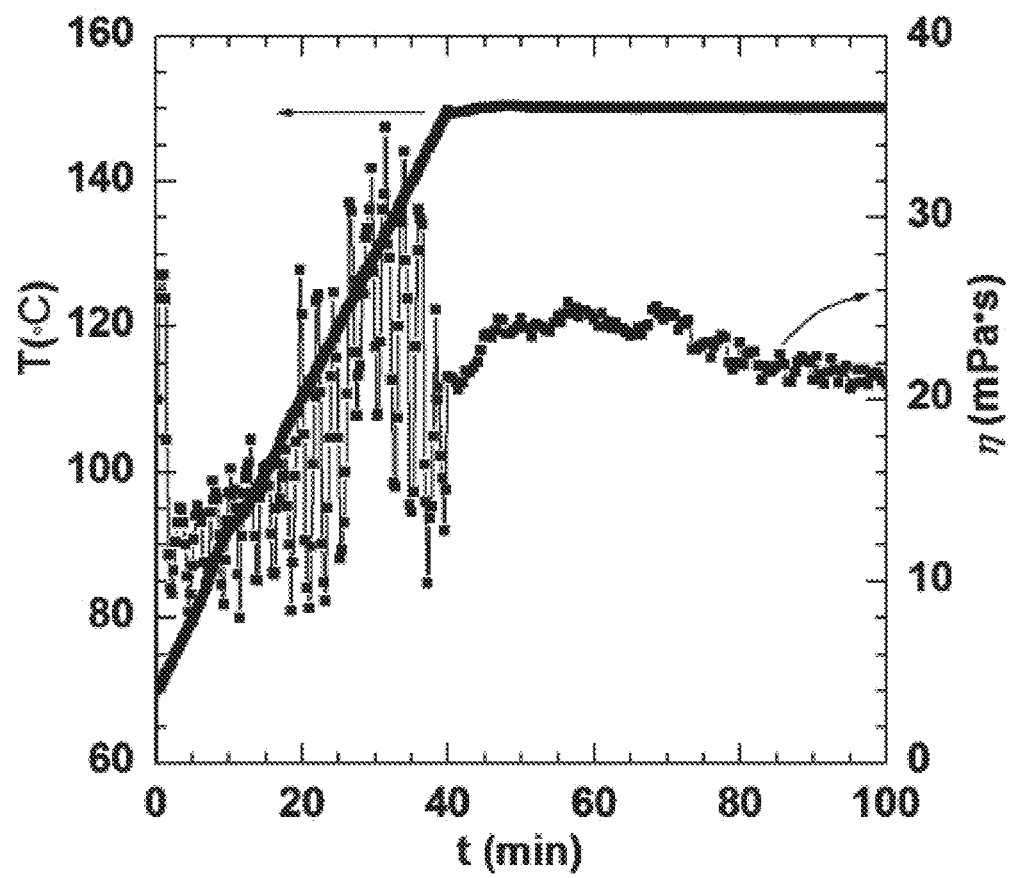
FIG. 12 shows the rheological behavior of a 3.0% N-(octadecylaminopropyl)-N,N-dimethyl tertiary amine hydrochloride solution in a 10% HCl solution at 150° C.

(3) The N-(octadecylaminopropyl)-N,N-dimethyl tertiary amine was mixed with a 10% HCl solution; and the mixture was thoroughly stirred at 50° C. for 24 h to obtain N-(octadecylaminopropyl)-N,N-dimethyl tertiary amine hydrochloride, where the N-(octadecylaminopropyl)-N,N-dimethyl tertiary amine had a molar ratio of 1:2 with $H^+$ in the 10% HCl solution. Then, the N-(octadecylaminopropyl)-N,N-dimethyl tertiary amine hydrochloride was mixed with a 10% HCl solution to obtain a self-diverting acid of N-(octadecylaminopropyl)-N,N-dimethyl tertiary amine hydrochloride, where the N-(octadecylaminopropyl)-N,N-dimethyl tertiary amine hydrochloride had a concentration of 3% in the acid solution. The viscosity of the acid system was tested at different temperatures by Anton Paar rheometer and the supporting PR170/XL rotor/drum system thereof. The relationship of the viscosity of the obtained self-diverting acid system with temperature and time was tested at a shear rate of 170 $s^-$. The results are shown in FIG. 12. It can be seen that, when the temperature is stabilized at 150° C., the viscosity of the acid solution is relatively stable and greater than 20 mPa·s, indicating that the ultra-long-chain VES obtained in this example has excellent temperature-resistance as a thickener.

Example 3

(1) 21.23 g (0.05 mol) of octacosanoic acid (commonly known as "montanic acid") and 9.76 g (0.075 mol) of N,N-diethylpropanediamine (n=2, $R_2$ and $R_3$ were ethyl groups) were weighed and added to a three-necked flask. The mixture was gradually heated to 160° C. and reacted for 11 h. The reaction was stopped and the reaction solution was transferred to an acetone solution after the reaction solution was cooled to room temperature. The resulting solution was stirred, filtered, and lyophilized to obtain a white solid powder, namely, N-(octacosylamidopropyl)-N,N-diethyl tertiary amine.

(2) The obtained N-(octacosylamidopropyl)-N,N-diethyl tertiary amine was added to a 500 mL round-bottom flask and 100 mL of THF was added to dissolve the solid. After the solid was completely dissolved, the resulting solution was cooled to 0° C. and a solution of $NaBH_4$ in THF was added dropwise. The mixture was then heated to 80° C. and reacted for 36 h. After the reaction was completed, deionized water, a 15% NaOH solution, and deionized water were added in sequence to the obtained reaction solution to quench the reaction. The resulting solution was filtered and the filtrate was dried over anhydrous $MgSO_4$ and filtered once again. The final filtrate was subjected to rotary evaporation to remove the solvent to obtain N-(octacosylaminopropyl)-N,N-diethyl tertiary amine, where the N-(octacosylamidopropyl)-N,N-diethyl tertiary amine and the $NaBH_4$ were used at a molar ratio of 1:2.

(3) The N-(octacosylaminopropyl)-N,N-diethyl tertiary amine was mixed with a 15% $H_2SO_4$ solution and a 10% HCl solution separately, where the N-(octacosylaminopropyl)-N,N-diethyl tertiary amine had a molar ratio of 1:2 with $H^+$ in the 15% $H_2SO_4$ or 10% HCl solution. The resulting mixtures were thoroughly stirred at 50° C. for 24 h to obtain N-(octacosylaminopropyl)-N,N-diethyl tertiary amine sulfate and N-(octacosylaminopropyl)-N,N-diethyl tertiary amine hydrochloride, respectively. Then the N-(octacosylaminopropyl)-N,N-diethyl tertiary amine sulfate and N-(octacosylaminopropyl)-N,N-diethyl tertiary amine hydrochloride were respectively mixed with a 15% $H_2SO_4$ solution and a 10% HCl solution to obtain a self-diverting acid based on N-(octacosylaminopropyl)-N,N-diethyl tertiary amine sulfate and a self-diverting acid based on N-(octacosylaminopropyl)-N,N-diethyl tertiary amine hydrochloride, respectively.

Example 4

(1) 18.33 g (0.05 mol) of cis-15-tetracosenoic acid (commonly known as "nervonic acid") and 7.21 g (0.055 mol) of octanediamine (n=8, $R_2$ and $R_3$ were hydrogens) were weighed and added to a three-necked flask, and the mixture was gradually heated to 165° C. and reacted for 12 h; then the reaction was stopped, and the reaction solution was transferred to an acetone solution after the reaction solution was cooled to room temperature; and the resulting solution was stirred, filtered, and lyophilized to obtain a white solid powder, namely, N-(cis-tetracosa-15-alkenyl-amidooctyl) amine.

(2) The obtained N-(cis-tetracosa-15-alkenyl-amidooctyl) amine was added to a 500 mL round-bottom flask, and 100 mL of THF was added to dissolve the solid; and after the solid was completely dissolved, the resulting solution was cooled to 0° C. and a solution of $LiBH_4$ in THF was added dropwise. The mixture was then heated to 80° C. and reacted for 36 h. After the reaction was completed, deionized water, a 15% NaOH solution and deionized water were added in sequence to the obtained reaction solution to quench the reaction. The resulting solution was then filtered and the filtrate was dried over anhydrous $MgSO_4$ and filtered once again. The final filtrate was subjected to rotary evaporation to remove the solvent to obtain N-(cis-tetracosa-15-alkenyl-aminooctyl)amine, where the N-(cis-tetracosa-15-alkenyl-amidooctyl)amine and the $LiBH_4$ were used at a molar ratio of 1:2.

(3) The N-(cis-tetracosa-15-alkenyl-aminooctyl)amine was mixed with a 10% $CH_3COOH$ solution, where the N-(cis-tetracosa-15-alkenyl-aminooctyl)amine had a molar ratio of 1:2 with $H^+$ in the 10% $CH_3COOH$ solution. The resulting mixture was thoroughly stirred at 50° C. for 24 h to obtain N-(cis-tetracosa-15-alkenyl-aminooctyl)amine acetate. Then, the N-(cis-tetracosa-15-alkenyl-aminooctyl) amine acetate was mixed with a 10% $CH_3COOH$ solution to obtain a self-diverting acid based on N-(cis-tetracosa-15-alkenyl-aminooctyl)amine acetate.

The above descriptions are merely preferred implementations of the present invention, and should not be construed as excluding other examples. It should be understood that the present invention is not limited to the form disclosed herein, and can be used in various other combinations, modifications and environments. Modifications can be made within the scope of the concept described herein through the above teachings or techniques or knowledges in related fields. Modifications and changes made by those skilled in the art without departing from the spirit and scope of the present invention should fall within the protection scope of the appended claims of the present invention.

What is claimed is:

1. A viscoelastic surfactant (VES) for a self-diverting acid under high temperature, wherein the VES has the following structural formula:

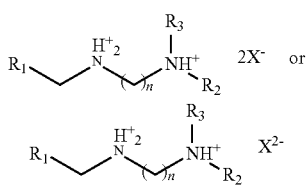

wherein n is saturated hydrocarbon with 2 to 8 carbon atoms;

$R_1$ is saturated alkyl with 20 to 28 carbon atoms or cis-22 carbon-13-alkenyl or cis-24 carbon-15-alkenyl;

$R_2$ and $R_3$ are independently methyl, ethyl or hydrogen, and $R_2$ and $R_3$ are the same or different;

$X^-$ is $Cl^-$, $Br^-$, $F^-$, $HCOO^-$, or $CH_3COO^-$; and $X^{2-}$ is $CO_3^{2-}$ or $SO_4^{2-}$.

2. A preparation method for preparing the VES for the self-diverting acid under high temperature according to claim 1, comprising the following steps:

S1: adding a fatty acid and an organic amine to a reactor to form a S1 mixture, and heating the S1 mixture to 160° C. to 170° C.; conducting a S1 reaction for 11 h to 13 h and then stopping the S1 reaction to obtain a S1 reaction solution; pouring the S1 reaction solution into a cold acetone solution after the S1 reaction solution is cooled to 25° C. to 35° C., and stirring a resulting solution; then conducting a filtration to obtain a solid, and washing the solid obtained 2 to 3 times with acetone; and conducting lyophilization to obtain a white solid intermediate; wherein the organic amine and the fatty acid are used at a molar ratio of (1.1-1.5):1;

S2: dissolving the white solid intermediate in tetrahydrofuran (THF) to obtain an intermediate solution, and adding the intermediate solution dropwise to a solution of a metal hydride in THF at 0° C. to 5° C. to form a S2 solution; heating the S2 solution to 65° C. to 85° C., and conducting a S2 reaction for 24 h to 36 h to obtain a S2 reaction solution; adding deionized water, a NaOH solution with a mass concentration of 10% to 20% and deionized water in sequence to the S2 reaction solution after the S2 reaction is completed; then conducting a first filtration, drying a first filtrate, and conducting a second filtration for the first filtrate; and removing solvent from a second filtrate obtained in the second filtration to obtain a fatty amine; wherein, the white solid intermediate and the metal hydride are used at a molar ratio of 1:(2.0-2.5); and the deionized water is added a first time to quench the metal hydride, then the NaOH solution is added to remove metal ions, and then the deionized water is added a second time to ensure that the metal hydride is completely quenched; and S3: mixing the fatty amine with an acid solution having a mass concentration of 10% to 20% to obtain a S3 solution, and thoroughly stirring the S3 solution to protonate the fatty amine forming the VES, wherein the fatty amine has a molar ratio of 1:2 with hydrogen ions in the acid solution.

3. The preparation method according to claim 2, wherein the fatty acid is a combination of at least one or more of saturated or unsaturated fatty acids having 20 to 28 carbon atoms.

4. The preparation method according to claim 2, wherein the organic amine comprises a combination of one or more of N,N-dimethylethylenediamine, N,N-dimethyl-1,3-propanediamine, N,N-dimethyl-1,4-butanediamine, N,N-diethylethylenediamine, N,N-diethyl-1,3-propanediamine, ethylenediamine, propanediamine, butanediamine, pentanediamine, hexamethylenediamine, heptanediamine and octanediamine.

5. The preparation method according to claim 2, wherein the metal hydride comprises a combination of one or more of $LiAlH_4$, $LiBH_4$ and $NaBH_4$.

6. The preparation method according to claim 2, wherein the acid solution comprises a combination of one or more of a HCl solution, a HBr solution, a HF solution, a $H_2SO_4$ solution, a $H_2CO_3$ solution, a HCOOH solution and a $CH_3COOH$ solution.

7. The preparation method according to claim 2, wherein, during the S1 reaction, circulating water cooling is continuously conducted to have the organic amine refluxed.

8. A method of using the VES of claim 1, comprising a step of using the VES as a thickener by mixing the VES with a viscoelastic self-diverting acid system.

9. The method according to claim 8, wherein the mixing the VES with a viscoelastic self-diverting acid system comprising mixing the VES with an acid solution having a mass concentration of 10% to 20%, wherein the acid solution having the mass concentration of 10% to 20% comprises a combination of one or more of a HCl solution, a HBr solution, a HF solution, a $H_2SO_4$ solution, a $H_2CO_3$ solution, a HCOOH solution and a $CH_3COOH$ solution, and the acid solution having the mass concentration of 10% to 20% is used at an amount allowing the VES as the thickener to have a mass concentration of 1% to 3% in an obtained viscous acid solution.

10. The viscoelastic surfactant (VES) of claim 1, wherein the VES is selected from a group consisting of N-(cis-docosa-13-alkenyl-amidopropyl)-N,N-dimethyl tertiary amine sulfate, N-(cis-docosa-13-alkenyl-amidopropyl)-N,N-dimethyl tertiary amine hydrochloride, N-(octacosylaminopropyl)-N,N-diethyl tertiary amine hydrochloride, N-(octacosylaminopropyl)-N,N-diethyl tertiary amine sulfate, and N-(cis-tetracosa-15-alkenyl-aminooctyl)amine acetate.

11. The viscoelastic surfactant (VES) of claim 1, wherein the VES in a solution of a self-diverting acid at a temperature of up to 150° C. has a viscosity of at least 80 mPa·s.

12. The viscoelastic surfactant (VES) of claim 1, wherein the VES in a solution of acid has a reaction rate that is slower than a solution of acid without the VES.

\* \* \* \* \*